(12) United States Patent
Tiltman et al.

(10) Patent No.: US 8,910,743 B2
(45) Date of Patent: Dec. 16, 2014

(54) ACOUSTIC REFLECTORS

(75) Inventors: Carl Peter Tiltman, Weymouth (GB); Andrew Malcolm Tulloch, Reading (GB)

(73) Assignee: Subsea Asset Location Technologies Limited, Dorset (GB)

( * ) Notice: Subject to any disclaimer, the term of this patent is extended or adjusted under 35 U.S.C. 154(b) by 43 days.

(21) Appl. No.: 13/808,491

(22) PCT Filed: Jul. 11, 2011

(86) PCT No.: PCT/GB2011/051298
§ 371 (c)(1),
(2), (4) Date: Jan. 4, 2013

(87) PCT Pub. No.: WO2012/007742
PCT Pub. Date: Jan. 19, 2012

(65) Prior Publication Data
US 2013/0105243 A1    May 2, 2013

(30) Foreign Application Priority Data

| Jul. 16, 2010 | (GB) | 1011939.4 |
| Sep. 17, 2010 | (GB) | 1015563.8 |
| Sep. 20, 2010 | (GB) | 1015705.5 |
| Sep. 21, 2010 | (GB) | 1015815.2 |
| Sep. 23, 2010 | (GB) | 1015952.3 |
| Dec. 3, 2010  | (GB) | 1020535.9 |
| Jan. 18, 2011 | (GB) | 1100753.1 |
| Jan. 18, 2011 | (GB) | 1100759.8 |
| Jan. 25, 2011 | (GB) | 1101278.8 |
| Jan. 25, 2011 | (GB) | 1101279.6 |
| Feb. 18, 2011 | (GB) | 1102847.9 |
| May 9, 2011   | (GB) | 1107588.4 |

(51) Int. Cl.
*G01V 1/04* (2006.01)
*G01V 1/38* (2006.01)
*G01V 1/00* (2006.01)

(52) U.S. Cl.
USPC ............................................ 181/110; 181/120

(58) Field of Classification Search
USPC ......... 181/110, 119, 120, 290, 293, 295, 175; 367/1, 2, 3, 131, 141, 151, 171
See application file for complete search history.

(56) References Cited

U.S. PATENT DOCUMENTS

| 2,465,993 | A | * | 4/1949 | Beechlyn | 367/131 |
| 2,888,675 | A | * | 5/1959 | Pratt et al. | 342/8 |
| 3,153,235 | A | * | 10/1964 | Chatelain | 342/8 |
| 3,195,677 | A | * | 7/1965 | Hillery et al. | 181/175 |
| 3,224,001 | A | * | 12/1965 | Radnofsky et al. | 342/8 |
| 3,447,627 | A | * | 6/1969 | Bellace et al. | 181/175 |
| 3,464,057 | A |   | 8/1969 | Hayner et al. |  |
| 3,598,199 | A | * | 8/1971 | Mertens et al. | 181/175 |
| 3,599,747 | A | * | 8/1971 | Hansen et al. | 181/212 |
| 3,806,927 | A | * | 4/1974 | Lane, Jr. | 342/7 |
| 3,901,352 | A | * | 8/1975 | Cluzel | 181/175 |
| 3,965,234 | A | * | 6/1976 | Lane, Jr. | 264/275 |
| 4,176,355 | A |   | 11/1979 | Harris |  |
| 4,673,934 | A | * | 6/1987 | Gentry et al. | 342/8 |
| 4,901,081 | A | * | 2/1990 | Bain et al. | 342/8 |
| 4,980,688 | A | * | 12/1990 | Dozier, Jr. | 342/9 |
| 4,982,386 | A |   | 1/1991 | Henriquez |  |
| 5,099,457 | A | * | 3/1992 | Giannotta et al. | 367/131 |
| 5,454,742 | A | * | 10/1995 | Robertson | 441/20 |
| 5,822,272 | A |   | 10/1998 | Ream, Jr. |  |
| 6,570,545 | B1 | * | 5/2003 | Snow et al. | 343/915 |
| 8,077,539 | B2 | * | 12/2011 | Smith et al. | 367/2 |
| 8,162,098 | B2 | * | 4/2012 | Emery et al. | 181/175 |
| 2008/0111448 | A1 |   | 5/2008 | Smith et al. |  |
| 2011/0266089 | A1 | * | 11/2011 | Tiltman et al. | 181/294 |
| 2012/0188844 | A1 | * | 7/2012 | Tiltman et al. | 367/2 |

FOREIGN PATENT DOCUMENTS

| EP | 0 291 892 | 11/1988 |
| GB | 1521592 | 8/1978 |
| GB | 2 437 016 | 10/2007 |
| GB | 2 458 810 | 10/2009 |

| WO | WO 2006/075167 | 7/2006 |
| WO | WO 2010/082082 | 7/2010 |
| WO | WO 2011/012877 | 2/2011 |

OTHER PUBLICATIONS

International Preliminary Report on Patentability issued Jan. 22, 2013 in PCT/GB2011/051298.
International Search Report for PCT/GB2011/051298 mailed Aug. 30, 2012.
D. Folds et al., "Target Strength of Liquid-Filled Spheres", Journal of the Acoustical Society of America, vol. 73, No. 4, Apr. 1, 1983, pp. 1147-1151.
G. Kaduchak et al., "Relationship Between Material Parameters and Target Strength of Fluid-Filled Spherical Shells in Water: Calculations and Observations", IEEE Journal of Oceanic Engineering, vol. 23, No. 1, Jan. 1, 1998, 5 pages.

* cited by examiner

*Primary Examiner* — Edgardo San Martin
(74) *Attorney, Agent, or Firm* — Nixon & Vanderhye P.C.

(57) ABSTRACT

An acoustic reflector primarily for underwater use comprising a shell surrounding a core in which holes are provided in the shell to allow air and water freely to enter and leave the interior of the shell when the reflector is immersed in water. Various embodiments are described including the use of a metal shell matched to a water core, the use of a mounting bar, provision of a frame to reflect acoustically alpha numeric characters, a soluble plug to delay operation of the reflector, and coating the reflector with polyurethane to limit damage. Also proposed is a pulse pattern to improve the identification of an acoustic reflector in some circumstances. Designs of reflectors particularly suitable for use with the relatively low frequency sonars found in the fishing industry with an aluminum or aluminum alloy shell are described, as are reflectors with a non-metal shell suitable for use with the higher frequency sonars in the underwater exploration industry. The reflectors can be spherical, toroidal, ovoid, or cylindrical provided that they have at least on circular cross section. A particularly important development with the current invention is the ability to mark and trace underwater non-ferromagnetic pipes.

30 Claims, 20 Drawing Sheets

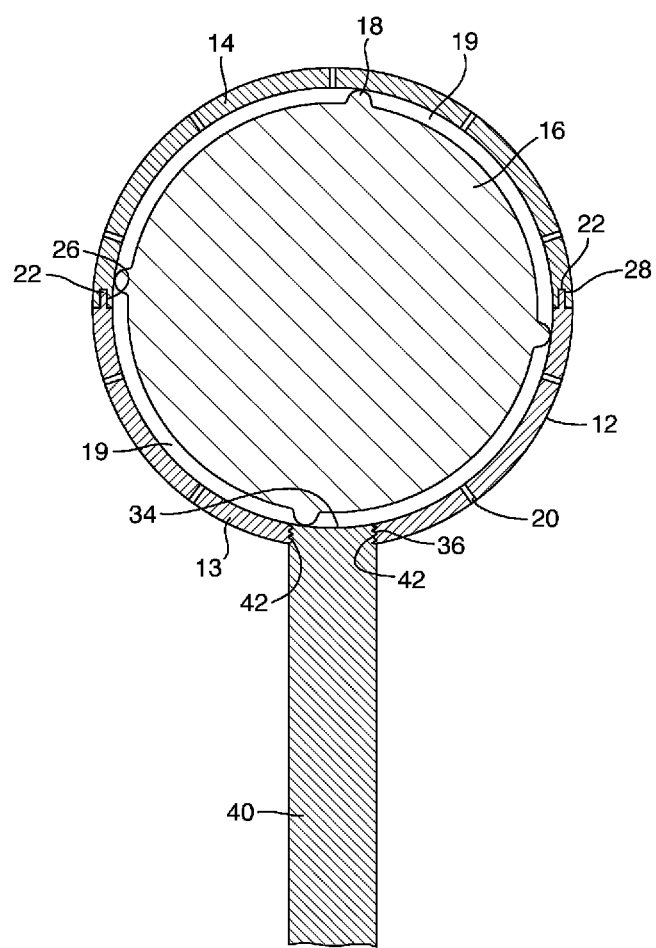

ACOUSTIC REFLECTORS

This application is the U.S. national phase of International Application No. PCT/GB2011/051298 filed 11 Jul. 2011 which designated the U.S. and claims priority to GB 1011939.4, filed 16 Jul. 2010, GB 1015563.8 filed 17 Sep. 2010, GB 1015705.5 filed 20 Sep. 2010, GB 1015815.2 filed 21 Sep. 2012, GB 1015952.3 filed 23 Sep. 2012, GB 1020535.9 filed 3 Dec. 2010, GB 1100753.1 filed 18 Jan. 2011, GB 1100759.8 filed 18 Jan. 2011, GB 1101278.8 filed 25 Jan. 2011, GB 1101279.6 filed 25 Jan. 2011, GB 1102847.9 filed 18 Feb. 2011, and GB 1107588.4 filed 9 May 2011, the entire contents of each of which are hereby incorporated by reference.

This invention relates to passive acoustic reflectors and markers used under water. Such reflectors may be used, for example, to mark objects and locations of interest underwater, underwater navigation channels etc.

Passive acoustic reflectors for use underwater are known, for example, from WO 2006/075167 A (THE SECRETARY OF STATE FOR DEFENCE) Jul. 20, 2006 and WO 2009/122194 A (THE SECRETARY OF STATE FOR DEFENCE) Aug. 10, 2009. In these publications a passive acoustic reflector for use underwater has a shell surrounding a core, said shell being capable of transmitting acoustic waves, incident on the shell into the core to be focused and reflected from an area of the shell located opposite to the area of incidence so as to provide a reflected acoustic signal output from the reflector, characterised in that the core is in the form of a sphere or right cylinder and is formed of one or more concentric layers of a material having a wave speed of from 840 to 1500 ms$^{-1}$ and that the shell is dimensioned relative to the core such that a portion of the acoustic waves incident on the shell are coupled into the shell wall and guided therein around the circumference of the shell and then re-radiated to combine constructively with the said reflected acoustic signal output so as to provide an enhanced reflected acoustic signal output. Acoustic waves incident on the shell may, for example, have come from a sonar system.

However these prior art reflectors when applied in commercial environments have issues, in particular, the different coefficients of expansion as between the core and shell can lead to excess strain being imposed on shells as a result of the thermal expansion of the core if a reflector is left exposed to heat, for example, as occurs in tropical climates or when a reflector is left in the sun on a quayside or on board ship. Thermal expansion of the core has led to failure of the shell. In addition other issues have arisen:

Filling an acoustic reflector with a suitable core material cannot be reliably achieved without shrinkage of the core mare material, leading to cracking and or voids in the core this causes inconsistent performance as between to apparently identical reflectors;

Acoustic coupling between the core and the shell is variable and is poor in some cases;

Health and safety regulations can limit the depth of deployment of such reflectors in water for fear that water seepage into the interior of the reflector would lead to an uncontained explosive failure when a reflector is raised to the surface: although proposes a solution to this problem, it is labour intensive in manufacture and thus comparatively expensive;

According to the present invention an acoustic reflector for use underwater and comprising a shell surrounding a core characterised in that the shell has one or more holes therein permitting water freely to enter and leave the inside of the shell when the reflector is deployed in water.

In this structure part of an incident acoustic wave may entering the shell passes through into the core and is reflected back from the shell wall opposite the entry into the core, and part may be guided within the shell itself around the core to combine constructively with acoustic wave passing through the core and to be reradiated from the shell.

In one embodiment of the invention the core has a volume slightly less than the interior volume of the shell; on entry into water, water enters the interior of the shell between the core and the interior of the shell wall. In this construction, there is sufficient scope to enable the core to thermally expand when transported or stored in hot climates, but for sea water to take up the space caused by contraction of the core material when the reflector is immersed in sea water. Furthermore, as the reflector is brought back to the surface, any build-up pressure inside the shell is simply relieved through water flowing out of the hole(s), avoiding any risk of explosive failure of the shell.

It has been found, surprisingly, that the presence of water inside the shell between the shell and the core substantially improves acoustic coupling between the shell and the core and the reliability of the acoustic coupling.

Thus in a first embodiment of the invention, the core has a cross section slightly less than the corresponding cross section of the inside of the shell forming a gap between the core and the inside of the shell said gap being filled with water when the reflector in immersed in water.

In a reflector according to this first implementation of the invention, the core may further be characterised in having a plurality of raised portions on its surface, said raised portions contacting the inside of the shell holding the core in position with respect to the shell.

In such an embodiment the raised portions may preferably be in the form of pimples, the peak of the pimples contacting the inside of the shell when the reflector is at its designed operating temperature.

The raised portions are deformable, and absorb expansion and contraction of the core without imparting substantial stress to the shell.

Preferably the core itself is a deformable material, such as an elastomeric material.

As an alternative to the configuration in the immediately preceding paragraphs, the interior of the shell may have a plurality of inward projections contacting the surface of the core when the reflector is at its designed operating temperature.

The contact points between the core and the inside of the shell should be at least five in number to ensure stable positioning of the core with respect to the shell, but ten is in practice better.

The holes allow water freely to enter and leave the volume between the shell and core, and when the reflector is immersed in water, water entering between the shell and core drives out air that was present before immersion. In practice, a large number of small holes distributed around the shell have been found more effective than one or a few holes. 24 holes work well, but 48 will reduce further any tendency for air to become trapped between the shell and the core on immersion of the reflector.

Typically, the holes are 1 mm in diameter and the raised portions or pimples are designed to maintain a filled gap of 1.3 mm between the body of the core and the inner shell wall when the shell is at its designed operating temperature. The gap will be filled with water when the reflector is immersed in water.

For some applications it may be desirable that the reflector remains relatively invisible for a time after placement in the water. In order to achieve this using a reflector of the kind described herein, air has to be retained between the shell and the core until the time the reflector is intended to be detectable. By providing one larger hole, say 10 mm in diameter and ensuring that it is uppermost when the reflector is placed in the water; air is expelled rapidly when the plug therein dissolves.

As an alternative or, preferably, in addition to the provision of gap between shell and core as described above, the elastomeric core can be cast with a hole at its centre with a duct leading from the centre to the outside of the shell, again allowing free access of water to the hole. This has a similar effect to the arrangements in the previous paragraphs, allowing the elastomeric or other deformable material to expand safely into the hole when hot. As the elastomeric or other deformable material cools after immersion in water, water fills the hole including the space vacated by the contracting core. By changing the size of the hole in the core from one reflector to another, the reflecting characteristics of the reflectors with also be changed, allowing one reflector to be distinguished from another. The diameter of the central hole should not exceed 10% of a diameter of the reflector passing through the hole, otherwise the properties of the reflector will deteriorate. The duct itself should be about 10 mm in diameter to allow air to escape when the reflector is immersed in water. The central hole can be usefully used to carry small payloads, such as monitoring devices.

In a further embodiment as an alternative to or preferably in addition to the provision of a gap between shell and core as described above, the reflector may have a hole in opposite sides of the shell communicating with a duct through the centre of the shell allowing free access of water into and out of the duct. The use of a duct has a further potential advantage in that enables a number of reflectors to be strung together, or a reflector to be tethered to an underwater object without the need of nets or cages as described in WO2011/012877 or WO2011/012878.

In each of the above cases, best performance is obtained if the shell and core materials are chosen so that the ratio of the speed of sound wave transmission in the shell to the average speed of the wave transmission in the core is in the range 2.5 to 3.4 or a multiple thereof. Realisation that a multiple of this ratio will also provide excellent results will enable an aluminium shell or aluminium alloy shell to be used with relatively compressible elastomer core materials such as RTV12. Incompressible cores exacerbate the problems arising from differential expansion.

Preferably the ratio of the speed of sound wave transmission in the shell to the average speed of the wave transmission in the core is in the range of 2.74 to 3.4, inclusive or a multiple thereof.

Sea water itself has an acoustic speed of 1433 ms$^{-1}$ to 1500 ms$^{-1}$, depending on its salinity. When combined with a silicon based elastomeric material, say RTV12, which has an acoustic velocity of 1018 ms-1, the ratio of acoustic velocity in a 25% glass fibre reinforced polyphthalamide shell to that of the core is decreased very slightly and is very close to the ideal ratio. Indeed sea water between the inside of the shell and the core significantly improves the acoustic coupling between the shell and the core, leading to even better performance than expected.

The inventors have found that a shell manufactured with 25% glass fibre reinforced polyphthalamide with a silicon elastomeric core of RTV12 produces excellent reflection of incident acoustic waves at specific frequencies. 25% glass fibre reinforced polyphthalamide is sold under the trade name Zytel® HTN51G25HSL by E.I. du Pont de Nemours and Company. A similar glass fibre reinforced polyphthalamide is marketed under the trade mark Amadel by Solvey SA. Polyphthalamides with higher glass fibre content are obtainable and provide harder shells, but as the glass fibre content increases so does the brittleness of the final shell and the speed of acoustic transmission in the shell. For optimum performance, the latter must be matched by using a core having a higher wave speed than RTV12 itself.

Other suitable non-metals to form the shell include epoxy impregnated carbon fibre Kevlar® (aramid) fibre, Zylon® [poly(p-phenylene-2,6-benzobisoxazole) or PBO] fibre impregnated with epoxy resin, and epoxy impregnated polythene fibre (e.g. Dyneema®). By varying the amount of fibre in the composite the longitudinal acoustic velocity within the material can be adjusted to match the application. By using the information herein concerning the best ratio of shell to core acoustic velocity ratios, a core material can be selected to yield best performance.

The shell may also be metal. Of potential metal shells, aluminium and its alloys are particularly good as aluminium reflects about 50% of incident acoustic signals, the rest passing into the in the core and around the inside of the shell. The waves passing around the inside of the shell combine constructively with those passing into the core, which are reflected from the rear of the core, the acoustic waves being reradiated back towards the source of the radiation. Aluminium alloy 6061T6 has a longitudinal acoustic velocity of 6299 ms$^{-1}$ when combined with an RTV12, the sea water reduces the ratio of acoustic velocities of shell to core to close to six and within the ratio proposed. In the case of an aluminium or aluminium alloy core the presence of water between the shell and the core also significantly improves the acoustic coupling between the shell and the core, even more so than in the case of the polyphthalamide shell.

Realising the relationship between the longitudinal velocity in the shell to that of the core described herein, the core material is ideally one having an acoustic velocity of just over 1000 ms$^{-1}$; RTV12 silicon rubber fits this criterion perfectly. Thus there is no need to load elastomers with calcium carbonate to adjust the velocity of the core. Calcium carbonate loaded elastomers are inherently less flexible and able to deform with thermal expansion.

Previously too, it has been necessary to fuse, either by spin welding or solvent gluing the two hemispherical shell parts together to form a spherical shell and to provide pressure relief means whereby the explosive expansion decompression is avoided. In the reflector of the present invention any pressure build up in the reflector caused by trapped water is automatically avoided as water can leave the reflector through the holes. There is thus no need to spin weld or use sophisticated glues to join the parts of the shell together.

In a further embodiment, therefore, an acoustic reflector, having a shell surrounding a core and in which said shell comprises two hemispheres, is characterised in that the rim of one hemisphere has a tongue, and the rim of the other hemisphere has a groove, the tongue engaging in the groove when the two hemispheres are joined. One of the tongue or groove has a latching portion extending laterally therefrom and the other of the tongue or groove has a detent to receive the latching portion. When the tongue is engaged with the groove the latching portion will engage the detent to hold both parts of the shell together. Such a non-metal shell is much easier and cheaper to make than a non-metal shell that is glued or welded.

If for safety cases ability to fail under increased internal pressure is required to be demonstrated, the latch arrangement described in the previous paragraph can be designed to shear if the pressure within the shell increases to a pre-set figure. For a glass fibre reinforced polyphthalamide shell such as Zytel® HTN51G25HSL this may be set at about 70 to 100 psi.

Instead of a latch and detent, for low risk environments, the two parts of the shell can be simply held together by netting.

Metal shells such as those of aluminium and aluminium alloy shells are preferably made by using a simple tongue and groove joint between the two halves of the shell and gluing the two halves together using a conventional low cost two part epoxy adhesive such as Aradite®.

The reflectors are most commonly spherical, however tubular, ovoid, cylindrical and toroidal reflectors can been made; the only limitation on an alternative shape is that the surface of the reflectors which receive an incoming acoustic wave should be smooth and not scatter the incoming acoustic wave.

Unexpectedly, acoustic reflectors according to the invention will transmit and reflect incident acoustic waves at much lower much frequencies (below 80 KHz and as low as 4 KHz) than, say, the known reflectors.

In particular, at these lower frequencies, better performance, is achieved with an acoustic reflector having a shell material with high modulus of elasticity, say more than $15 \times 10^5$ Kg-cm$^{-2}$.

With a 300 mm diameter 8.8 mm thick 6061T6 aluminium alloy shell, which has a modulus of elasticity of $15 \times 10^5$ Kg-cm$^{-2}$ and RTV12 core an overall response of −3 dB has been obtained at 62 KHz, which is better than any other response recorded with an underwater passive acoustic reflector. Of potential metal shells, aluminium and its alloys are particularly good. Steel is problematic because of its tendency to rust in sea water, and a large part of the incident acoustic radiation is reflected from its front surface. Larger diameter spheres would perform even better, but are more expensive to make. Spheres which are less than 200 mm in diameter perform less well at low frequencies and 100 mm diameter is probably the lower limit for sub-sea operations as the frequency at which a reflector will respond increases markedly below this diameter.

At higher frequencies, above 100 KHz, shells with a lower modulus of elasticity, such as glass reinforced polyphthalamides should be used. An overall response of −4 dB has been achieved using a 200 mm diameter glass reinforced polyphthalamide shell with a RTV12 core and a 1.3 mm gap between the inner wall of the shell and the core at 160 KHz., with peak responses also occurring at higher frequencies.

The invention works using aluminium or aluminium alloy shell thicknesses between 6 and 30 mm, although at above 15 mm the weight and cost penalties are such that thicker shells are not sensible. Below 6 mm shells of aluminium and its alloys become too flexible. For 25% glass reinforced Zytel® shells the sensible shell thicknesses are 4 mm to 15 mm inclusive. A degree of optimisation is necessary for each design. However, for shells of aluminium and its alloys or 25% glass reinforced Zytel®, 8.8 mm seemingly is a good compromise. Optimisation is achieved by testing various reflectors of different diameters and shell thicknesses against the frequency of the acoustic waves of interest.

The core may be the silicon elastomer RTV12, although other elastomers may also be used.

Previously netting and cages have been proposed to locate the acoustic reflectors in place. However, in a further embodiment of the invention a bar is fitted to a hole in the shell of an acoustic reflector of the kind described above. The bar may be tapered at one end and glued or friction welded in place. Alternatively, and preferably, the bar is externally threaded at one end and said end is fitted to an internally threaded hole in the shell of an acoustic reflector of the kind described in this invention. This arrangement has a particular advantage since, because the pressure inside the shell is the same as the surrounding sea water, the bar does not require sealing to the shell. The treaded hole would be bigger than any other holes in the shell. The bar may be used as part of the means to hold the reflector in place as described below.

In each of the embodiments mentioned in the previous paragraph, the other end of the bar would be designed to fit to an object to be marked, or to some specific location. Typically this end of the bar would be externally threaded and may be screwed into a mounting point on an object, or to a plinth on the sea bed.

Ideally the bar is made of the same material as the shell to minimise disruption of acoustic wave travelling around the shell wall. However, if the shell is of metal such aluminium alloy, and the bar was of the same metal, care would be needed in mounting it on another metal object to be marked to avoid electrolytic corrosion.

Some sonar systems emit individual acoustic pulses that last for a long time; long pulses are used particularly in sonars which use a reflected signal to gather analytical information about a reflected target. When such sonars are used in conjunction with known reflectors, the returning signal directly reflected from the front shell of the reflector can mask the acoustic signal returned from acoustic waves that have entered the shell, resulting in loss of useful identification information concerning the reflector itself.

Therefore, an acoustic reflector is provided in conjunction with a pulsed underwater acoustic source wherein the pulse time and separation is less than twice the distance from the point of entry of the acoustic transmission into the core of the reflector divided by the acoustic velocity in the core. In the case of a spherical acoustic reflector the pulse time and separation is thus twice the diameter of the sphere divided by the acoustic velocity. In this way the reflected acoustic wave from the interior of the reflector will be "heard", and not dominated by reflections from the front of the shell. A shorter pulse of this kind may be combined with longer pulses, provided the short pulse occurs sufficiently often to enable the reflector concerned to be identified.

It had been found that in some applications, the acoustic reflectors can be very roughly handled prior to immersion in water, leading to damage to the shell. Such damage may lead to degraded performance of the reflector in use, or to splitting the shell altogether. This is particularly true of non-metallic shells. Thus in a further development of the invention the acoustic reflector is characterised in having a coat comprising of one or more layers of polyurethane around the outside of the shell.

Other features of the invention are set out in the claims.

FIGS. 1A, 1B, and 1C show components of an acoustic reflector made from aluminium alloy 6061T6 according to the invention;

FIG. 5 shows a section of an acoustic reflector as described in FIGS. 1 and 2 fitted with a mounting bar;

Figure 12A:
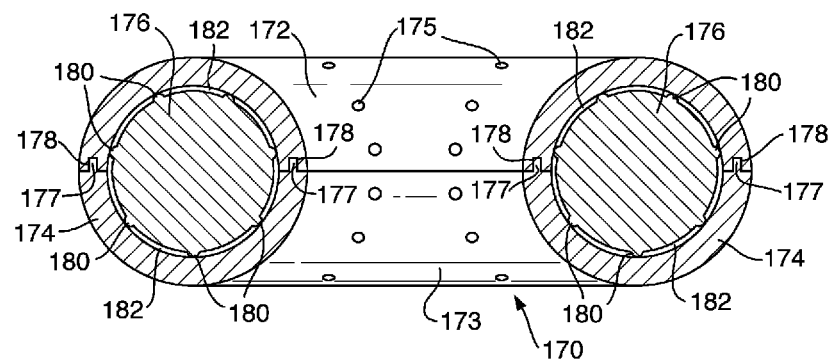
FIGS. 12A and 12B shows a toroidal marker according to the present invention.
Figure 12B:
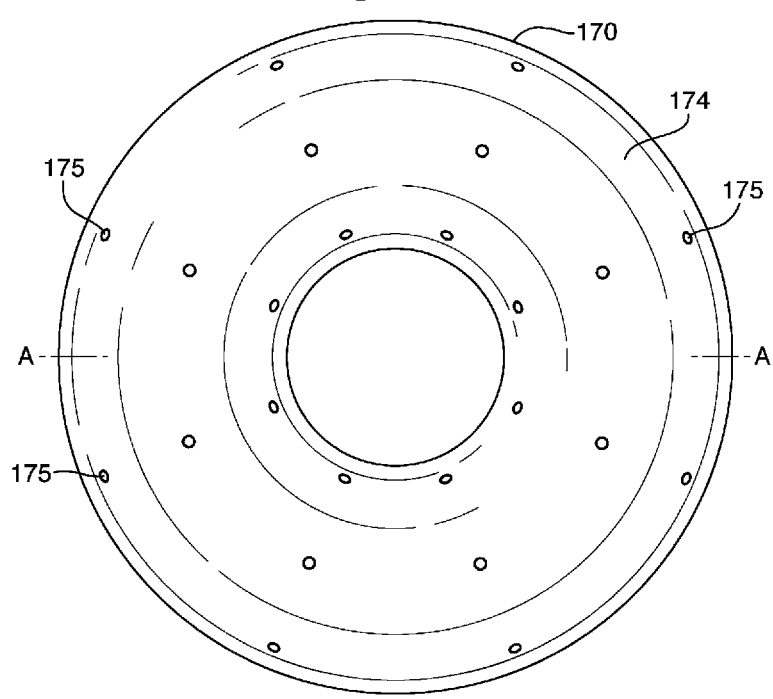
Figure 13:
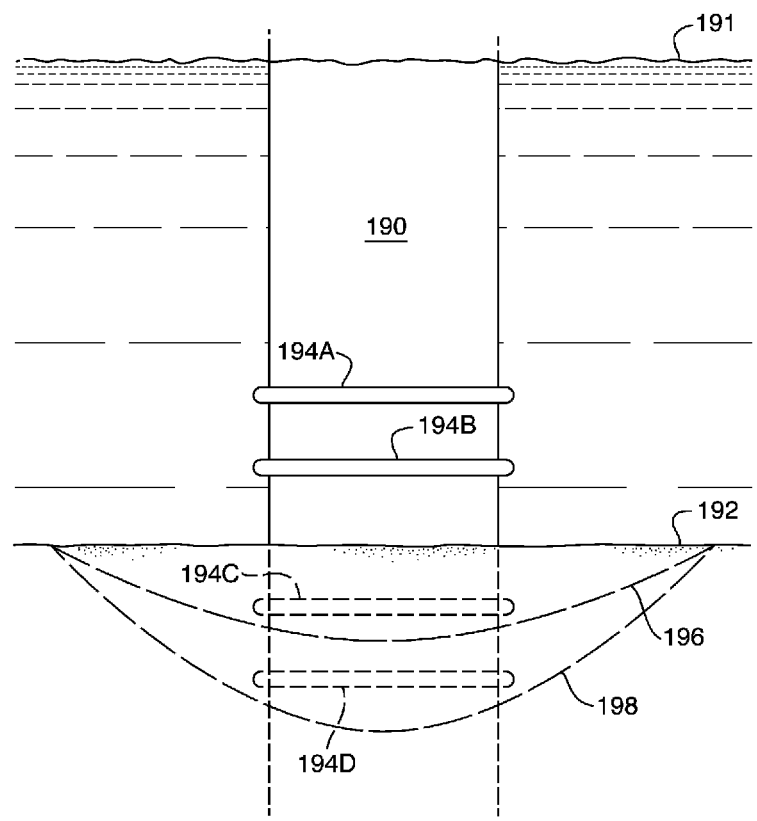

FIG. 12A being a section on the line A-A' of FIG. 12B;

FIG. 13 shows the use of a toroidal marker to monitor scouring.

Figure 1A:
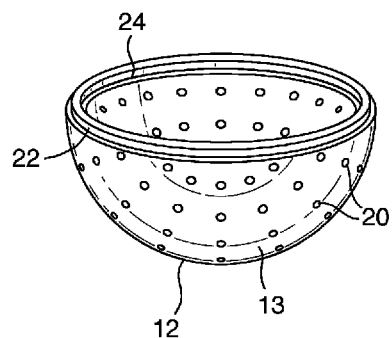
Figure 1B:
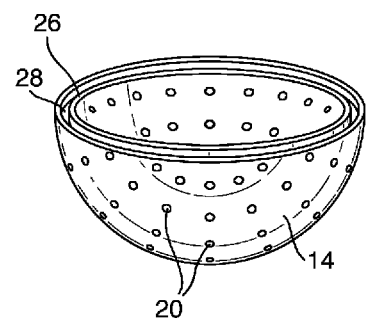
Figure 1C:
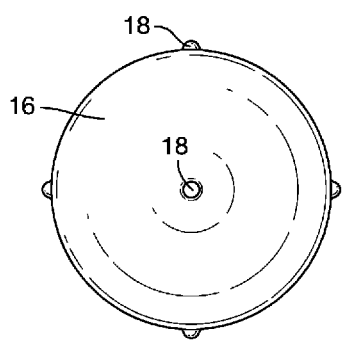
Figure 2:
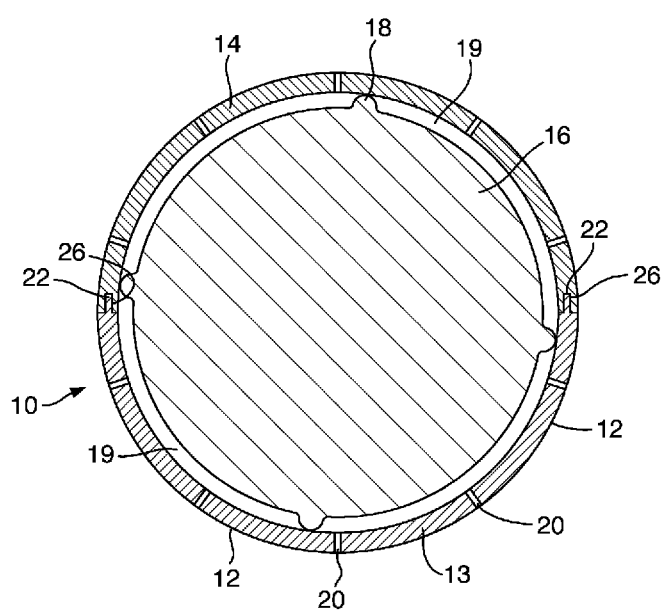
FIG. 2 is a cross section of the acoustic reflector made using the components shown in FIGS. 1A to 1C.
Figure 4A:
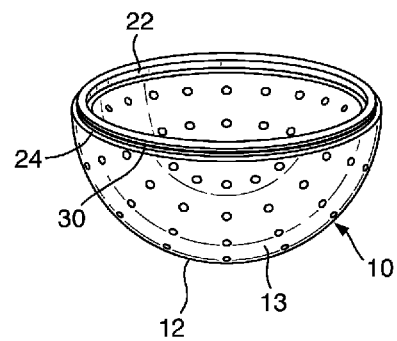
FIG. 4 shows the components of an alternative embodiment of the invention in which the material of the shell of the acoustic reflector comprises 25% glass reinforced polyphthalamide.
Figure 4B:
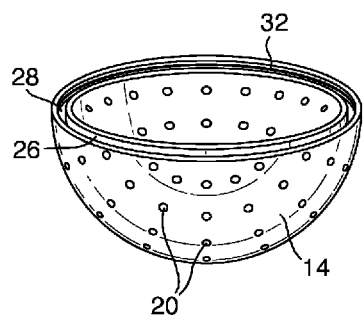
Figure 4C:
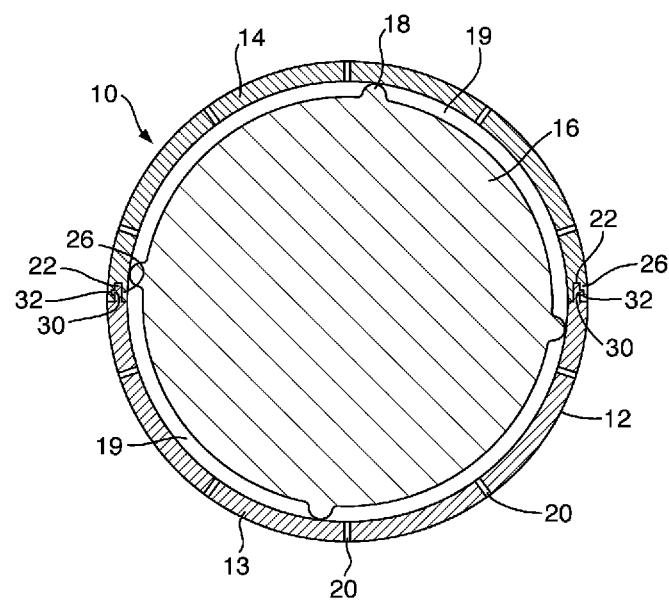
Figure 14:
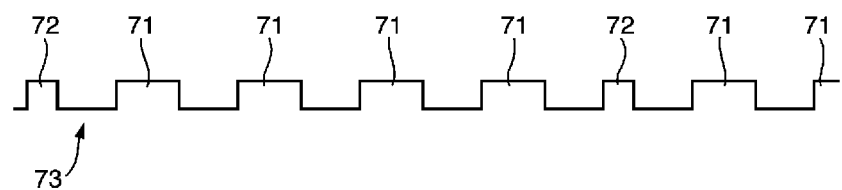
Figure 15:
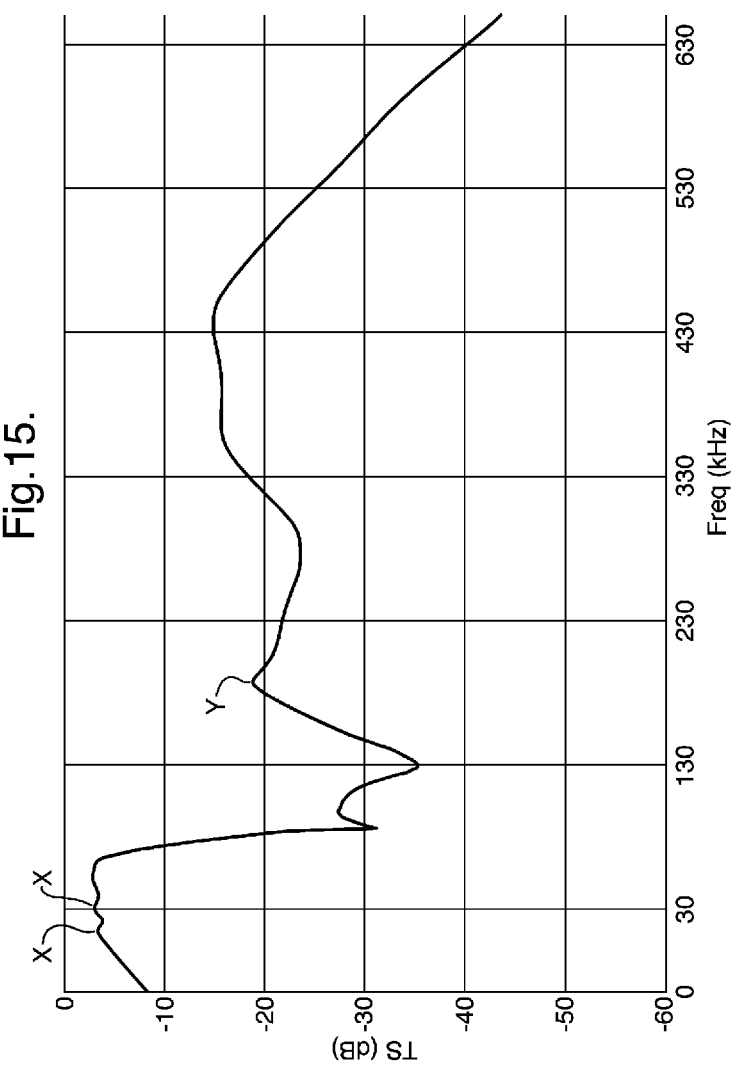
Figure 16:
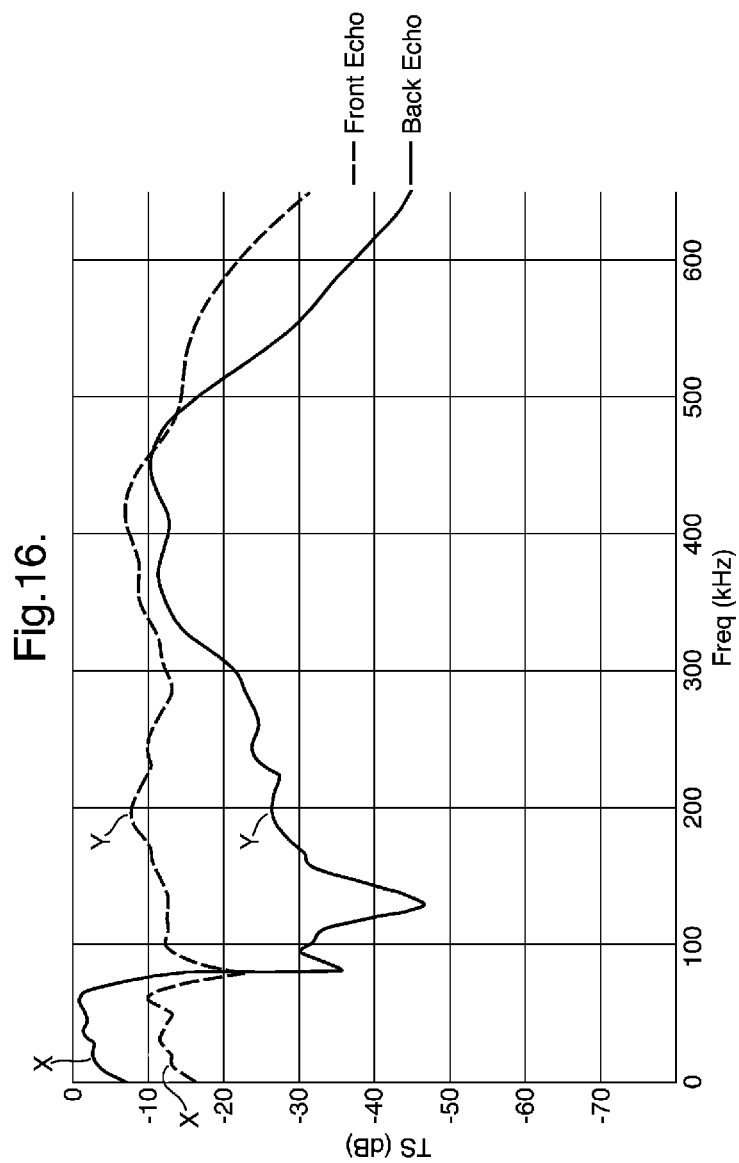
Figure 17:
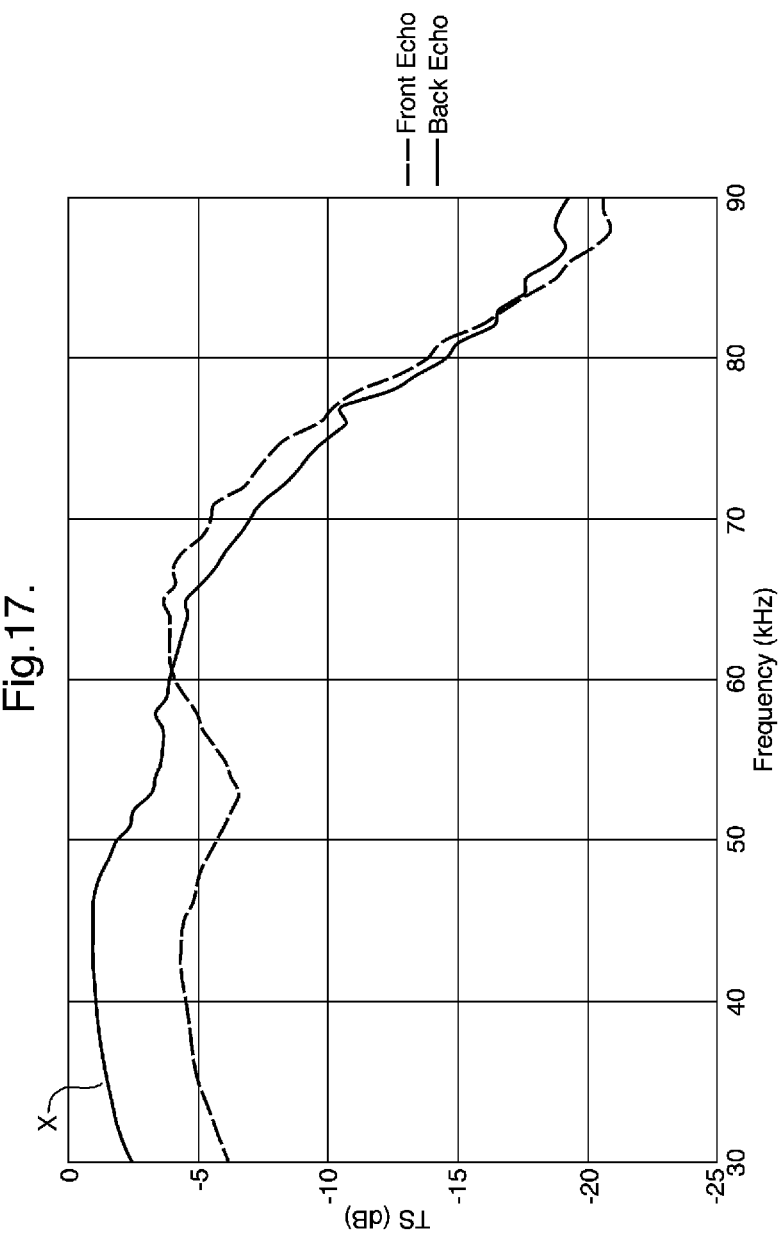
Figure 18:
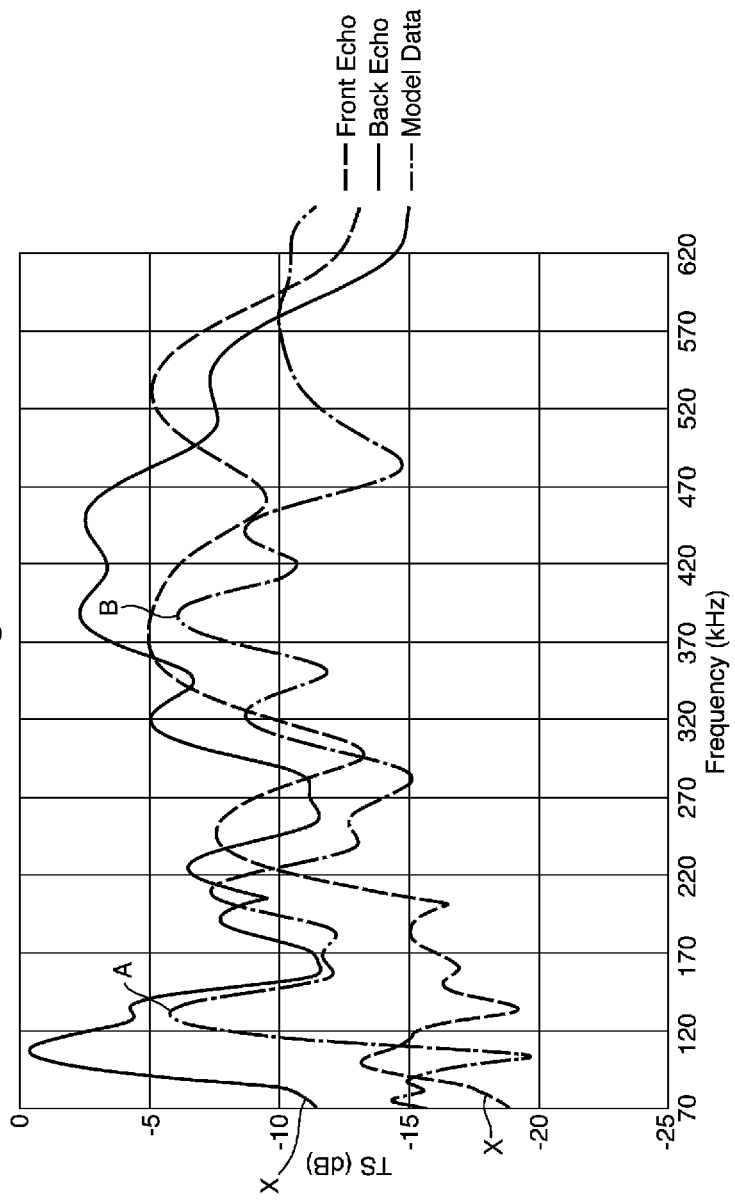
Figure 19:
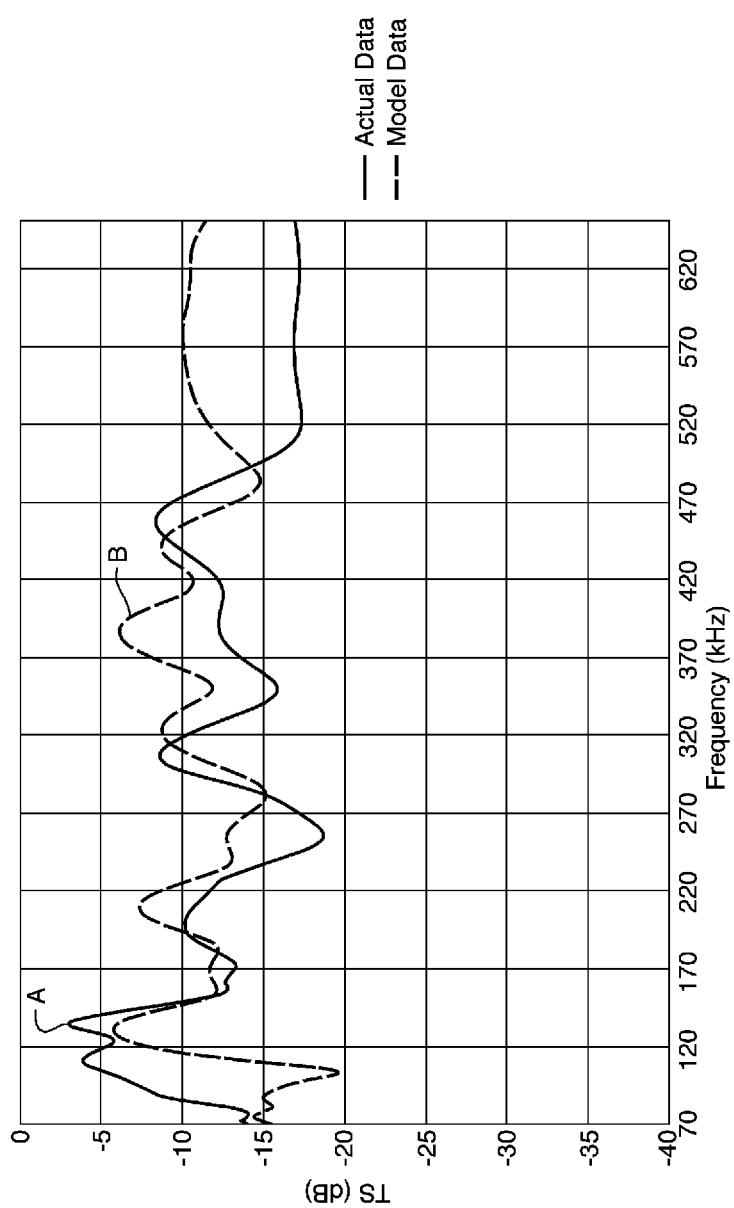

FIG. 14 illustrates the use of short transmission pulses from an acoustic source in combination with longer pulses to enable identification of an acoustic reflector;

FIG. 15 illustrates the response of an underwater acoustic reflector with an aluminium alloy (6061T6) shell and RTV12 core in accordance with this invention, constructed in accordance with FIGS. 1 and 2;

FIG. 16 compares the echoes at low frequencies from the front with the back of the reflector exemplified in FIG. 15;

FIG. 17 compares the echoes at various frequencies from the front with the back of the reflector exemplified in FIG. 4C at low frequencies;

FIG. 18 compares the echoes at various frequencies from the front with the back of the reflector exemplified in FIG. 4C at higher frequencies and compares the results with model data; and FIG. 19 is similar to FIG. 18 but shows the overall response of the reflector and compares it to model data.

In FIGS. 1A to 1C the components of an acoustic reflector (10 in FIG. 2) for use underwater according to this invention are shown. Two hemispheres 13 and 14 comprise the shell 12 of a spherical acoustic reflector. The hemispheres are made of aluminium alloy 6061T6. The core 16 of the reflector is cast RTV12 and is shown in FIG. 1C. The diameter of the core 16 is such that it is very slightly smaller, at ambient temperature, than the inside diameter of the shell when the two hemispheres 13 and 14 are assembled together. The core 16 has a plurality of upstanding pimples 18 distributed evenly around the outside of the core. In practice, a minimum of five pimples is needed, but eight to ten have been successfully used for manufacture. The pimples are about 1.3 mm high.

One or more holes 20 are provided in the hemispheres 13 and 14. It is preferred that a large number of small holes each 1 to 2 mm in diameter be provided to ensure that all the internal air is vented from the inside of the reflector when it is immersed in waters and for water to fill any gaps between the inside of the shell and the core. Two larger holes, about 10 mm in diameter could be used, but one hole alone risks being blocked when the reflector comes to rest on the sea bed. In this example altogether twenty four are provided, but spheres made with more than ten operate satisfactorily, although the larger number ensures improved water access and air expulsion on immersion of the reflector in water.

A tongue 22 is provided around the rim 24 of one of the hemispheres 13. A groove 26 is provided on the rim 28 of the other hemisphere 14 to receive tongue 22 when the hemispheres 13 and 14 are assembled together.

RTV12 for the core 16, is from a two part mix and initially is poured into a shaped mould to form the core with the pimples and cured in a conventional way. The mould is overfilled leaving a sprue to reduce the opportunity for fissures to form. The sprue is then cut off once the core has cured. Subsequently the RTV 12 core 16 is placed in one of the hemispheres, say 14. The other hemisphere, say 13, is then placed over the core 16 with the tongue 22 of hemisphere 13 engaging within the groove 26 associated with the hemisphere 14. This can be seen in more detail in FIG. 2. The pimples 18 hold the core 16 centrally within the shell 12, with a gap 19 between the inside of the shell 12 and the core 16.

When the assembled reflector is immersed in water, water enters through the holes 20 filing the gap 19. It should be noted that for clarity, the figures are not to scale, and in FIG. 2 the gap 19 is actually slimmer than would appear in the drawing being normally about 1.3 mm.

Although the core 16 is in this example RTV12, other elastomeric cores can be used, although their specific performance will vary from those shown in this specification.

The sphere, when assembled is glued using standard epoxy resin glue suitable for joining aluminium components: Araldite 2000 Plus™ is suitable. It is essential that all air be excluded from the joint.

It has been found helpful to coat the core 16 with an anti-fouling compound to prevent build-up of material in gap 19. There are currently ten anti-fouling compounds authorised for use in marine environments.

In theory, steel has the potential also form the shell of FIGS. 1 and 2, but this has been rejected firstly because a very high proportion of any incident acoustic wave is reflected from the front, leaving a relatively weak echo from the back, making the reflector hard to see with a sonar, and secondly because of corrosion problems under water. Brass appears more suitable but it is much more expensive and too heavy in use.

As indicated previously a degree of optimisation is necessary to achieve the best combination of shell thickness and shell diameter for any particular application. But a 300 mm spherical 6061T6 shell with a wall thickness of 8.8 mm works well at frequencies below 80 KHz, as seen in FIGS. 15 and 16.

Figure 3:
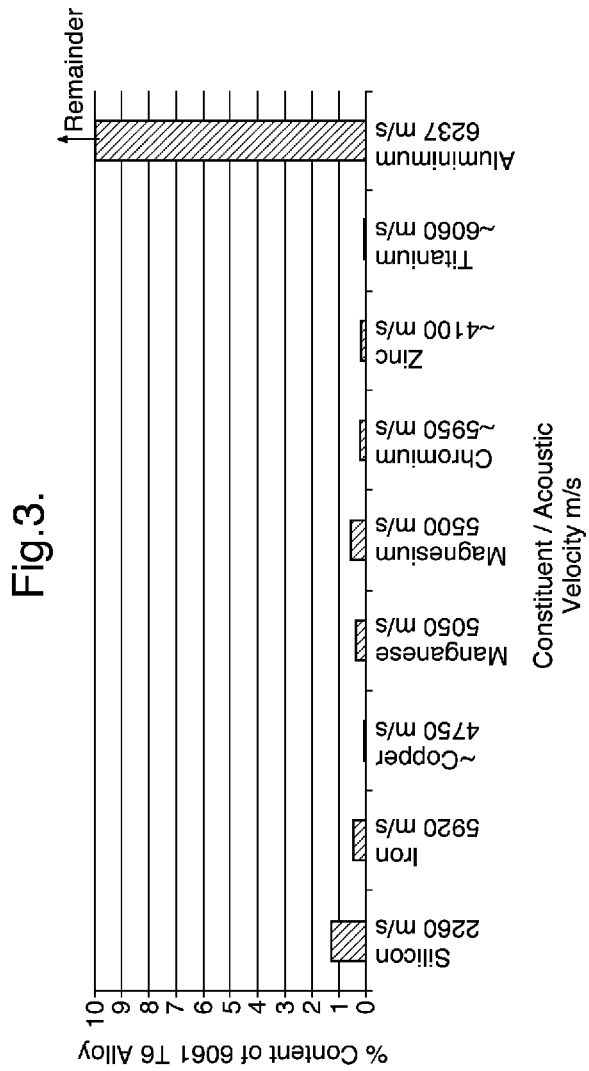
FIG. 3 illustrates the constituents of 6061T6 aluminium alloy.

FIG. 3 shows the constituents of aluminium alloy 6061T6. A number of constituents, silicon and zinc for example, have acoustic velocities substantially below that of aluminium. By increasing the content of those materials in the alloy, the acoustic velocity of a shell made of aluminium alloy can be reduced. Beryllium, on the other hand (not used in aluminium alloy 6061) has a much higher acoustic velocity and could be added to increase acoustic velocity if this was needed—it is not, however, a desirable option because of the very high cost of aluminium-beryllium alloys.

The combination of an aluminium alloy 6061T6 shell and an RTV12 core has a ratio of acoustic speed in the shell to the core of 6.11:1. The presence of water in the gap 19 (see FIG. 2) will reduce this to about 6.0, depending on the exact salinity of the water. Best performance is obtained if the shell and core materials are chosen so that the ratio of the speed of sound wave transmission in the shell to the average speed of the wave transmission in the core is in the range 2.5 to 3.4. It is found that a multiple of the ratio works well too, avoiding the need to use a core material other than unmodified RTV 12 in combination with aluminium or aluminium alloy, or the need to adjust the alloy content of the aluminium alloy away from one of the standard commercially available alloys. The performance of this reflector, as discussed with reference to FIGS. 15 and 16 below, clearly demonstrates that is particular ratio, which is a multiple of the preferred ratio 2.74 to 3.4 provides excellent, indeed un-expected, performance when interrogated by an incident acoustic waves below 100 KHz.

Moving on to FIGS. 4A to 4C, which illustrate the components of an acoustic reflector whose shell comprises 25% glass reinforced polyphthalamide sold under the trade name Zytel® HTN51G25HSL by E.I. du Pont de Nemours, the components are identical to those of FIGS. 1A to 1C save for the different shell materials, and the provision of a circumferential raised portion or latch 30 around one face of the tongue 22 and a corresponding detent 32 on a face of a corresponding wall of the groove 26 to receive the latch 30. When the two hemispheres 13 and 14 are assembled together around the core, the circumferential latch 30 engages in detent 32 as can be seen in FIG. 4C. The latch 30 can be constructed so that it will fail if the pressure inside the shell exceeds a pre-set minimum, say between 70 and 100 psi, allowing the two hemispheres 13 and 14 to part from one another, if this required for safety approval and certification. However failure of a reflector according to this invention as a result of build-up of pressure within the reflector itself has not been known. The same pressure relief effect, if needed, is achieved with the aluminium alloy construction of FIGS. 1 and 2 by the epoxy glue failing should pressure within the reflector exceed the same pre-set minimum.

The inventors have found that a shell manufactured with 25% glass fibre reinforced polyphthalamide as illustrated in FIG. 4 with a silicon elastomeric core of RTV 12 produces excellent reflection of incident acoustic waves at specific frequencies. 25% glass fibre reinforced polyphthalamide is sold under the trade name Zytel® HTN51G25HSL by E.I. du Pont de Nemours and Company. A similar glass fibre reinforced polyphthalamide is marketed under the trade mark Amadel by Solvey SA. Polyphthalamides with higher glass fibre content are obtainable and provide harder shells, but as the glass fibre content increases so does the brittleness of the final shell and the speed of acoustic transmission in the shell. For optimum performance, the latter must be matched by using a core having a higher wave speed than RTV12 itself.

Other suitable non-metals to form the shell of FIG. 4 include epoxy impregnated carbon fibre, Kevlar® (aramid) fibre, Zylon® [poly(p-phenylene-2,6-benzobisoxazole) or PBO] fibre impregnated with epoxy resin, and epoxy impregnated polythene fibre (e.g. Dyneema®). By varying the amount of fibre in the composite the speed of sound can be adjusted to match the application. By using the information herein concerning the best ratio of shell to core acoustic velocity ratios, a core material can be selected to yield best performance. Low cost low life expectancy shells using Nylon 6 are also possible, As indicated previously, a degree of optimisation is necessary to achieve the best combination of shell thickness and shell diameter for any particular application. But a 300 mm diameter spherical 25% glass fibre reinforced polyphthalamide shell, 8.8 mm thick, interrogated using comparatively low acoustic frequencies had front and back echoes as shown in FIG. 17. These are less that obtained using the aluminium alloy shell of FIGS. 1 and 2 but still significantly better than any competing product.

The reflector of FIG. 4 performed better than the 25% glass fibre reinforced polyphthalamide shell of WO2011/012877 this is as a result of the better coupling between shell and core obtained in this invention compared with that of the structure of WO2011/012877. At frequencies above 100 KHz, it also performed better than the reflectors of FIGS. 1 and 2, but less well at frequencies below 100 KHz.

With a non-metal shell damage has occurred to the shell when it is stored on-shore or on the deck of a vessel. This damage can be reduced by coating the shell with polyurethane, which is closely matched acoustically to sea water, although care must be taken to avoid blocking the holes.

In FIG. 5, the two hemispherical halves 13 and 14 of a reflector shell 12 of a spherical acoustic reflector in accordance with the invention are as described in FIGS. 1 and 2. Other identical features are not described in detail but can be identified with reference to FIGS. 1 and 2. One hemispherical half 13 of the shell 12 is provided with an internally threaded hole 34. The internal threads 36 of the hole co-operate with the external threads 42 of one end of bar 40. The other externally screw threaded end of the bar 40 may be screwed into a suitable internally threaded socket to mount the acoustic reflector in place. Ideally bar 40 is made of the same material as the shell 12 of the acoustic reflector.

In FIGS. 1 to 4 thermal expansion may be further accommodated by the distribution of a plurality of small gas bubbles in the core, the bubbles compressing to take up thermal expansion of the core.

Instead of the pimples 18 and gap 19 in FIGS. 1, 2 and 4 a plurality of fissures or indents can be provided in the outer surface of the core 16. Each of these fissures of indents is associated with one or more holes 20 in the shell through which air may enter and leave the fissures as the core expands and contracts thermally. Once in water, water enters and air is forced out of the fissures through the holes in the shell.

In FIG. 5, the two hemispherical halves 13 and 14 of a reflector shell 12 of a spherical acoustic reflector are as described in FIGS. 1 and 2. Other identical features are not described in detail but can be identified with reference to FIGS. 1 and 2. One hemispherical half 13 of the shell 12 is provided with an internally treaded hole 34. The internal threads 36 of the hole co-operate with the external threads 42 of one end of bar 40. The other externally screw threaded end of the bar 40 may be screwed into a suitable internally threaded socket to mount the acoustic reflector in place.

The bar 40 is made of the same material as the shell 12 of the acoustic reflector. Thus the bar 40 shown in FIG. 5 would be the aluminium alloy 6061T6; if the shell was of the kind shown in FIG. 4, the bar would be 25% glass reinforced polyphthalamide.

Figure 6:
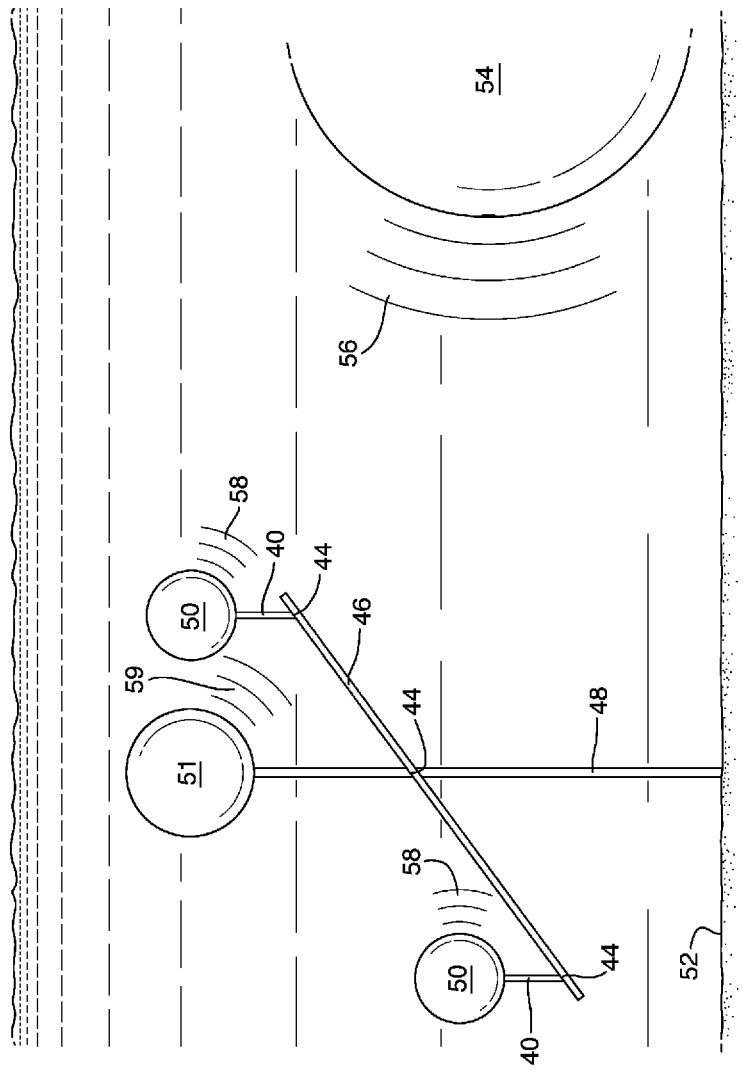
FIG. 6 shows the use of mounting bars in which acoustic reflectors according to the invention provide simple position information underwater.

FIG. 6 illustrates a sample use of the bar of FIG. 5. Two identical acoustic reflectors 50 of the kind described in FIG. 5 are mounted underwater by screwing bars 40 also of the kind shown in FIG. 5 into an internally threaded hole in the shell of these reflectors. The other ends are screwed into sockets 44 at each end of a cross arm 46 of a trident—like mounting device 48 fixed to the sea-bed 52, say, between the legs of an oil rig platform (not shown). A further, larger, acoustic reflector 51 of the same kind is mounted on a further upstanding bar 40 mounted in a further socket 44 on the cross arm 46 of the trident 48 mid-way between the two smaller acoustic reflectors 50. Reflector 51 is set slightly higher in the water than reflectors 50. Reflectors 50 and 51 are of the kind illustrated in FIGS. 1 and 2 with holes in the shell to allow free access of water into a gap between the core and the shell.

A sonar array 54 attached to a submersible addresses the acoustic reflectors 50 and 51 with a wide band sonar transmission 56. The frequency make up of reflected signals from the acoustic reflectors varies according to the diameter of the reflectors, the smaller reflectors providing a reflected acoustic wave 58 made up of generally higher frequencies than reflected acoustic waves 59 from the larger reflector 51. These signals can be analysed conventionally when received by the submersible, with the reflected acoustic waves' power and angles of incidence giving information concerning the distance of the reflectors 50 and 51. Knowledge of the dimensions of the trident 48 and the lengths of cross arm 46 and bars 40 can be used to compute, very accurately the position of the submersible with respect to trident 48.

This arrangement has one other interesting advantage. It is well known that short wavelength sonar signals attenuate much more rapidly than longer wavelength sonar signals. It is therefore clear that the reflected signal 59 from reflector 51 can be "heard" by the submersible at a much greater distance than the short wavelength reflected signals 58 from reflectors 50. Thus initial guidance of a submersible towards the target object marked by the trident 48 can be on the basis of the reflected acoustic signal 59 from reflector 51. As the submersible nears trident 48, reflections from the two smaller reflectors 50 will be obtained and final accurate steering of the submersible towards its objective achieved.

In another arrangement, a plurality acoustic reflectors of the kind described herein can be of the same size and mounted to form the outline of letter and/numbers. Thus a particular asset can be marked under water, say by reflecting the identification code in the form of the letter/number combination. If a side scan sonar is used for identifying the a letter number combination, the frame mounting the reflector arrangement for the letter/number concerned will need to be mounted at an angle to the vertical. Most side scan sonar systems are set to scan at about at around 45° to the horizontal; so for best identification with such sonar in use, the frame would be mounted in such a way that the letter/number outline to be reflected by the reflectors is also at 45° to the horizontal.

Figure 7:
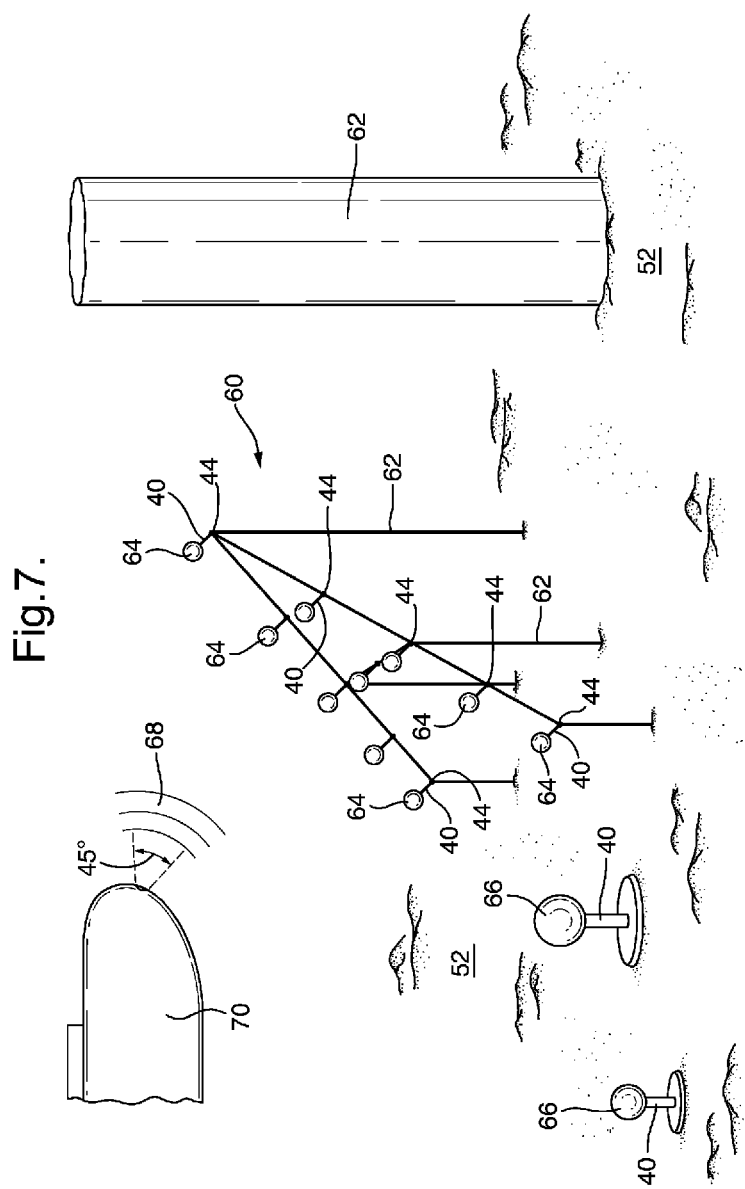
FIG. 7 shows the use of a bar in conjunction with the present invention to create an acoustic response as a letter form.

In FIG. 7, an A-shaped outline frame 60 is shown mounted on the sea floor 52 in front of part of a drilling rig 62, such that the plane of the letter A is at 45° to the horizontal. The frame 60 and the upright members 62 holding it in place on the sea floor are constructed of a plastic material (its actual character is not critical provided it is rigid, resistant to degradation in sea water and it has low acoustic reflectivity); polyurethane is suitable as this is almost transparent to underwater acoustic waves.

A series of internally threaded sockets 44 are mounted on top of the frame at points outlining the main shape of the letter A. The sockets receive the externally threaded end of a bar 40 of the kind described in FIG. 5.

The bars are perpendicular to the frame 60 of the A. The other end of the bars 40 are screwed into externally threaded holes of spherical acoustic reflectors 64 of the kind described in FIG. 5. Other similar reflectors 66 (which may be of a different diameter to reflectors 64) mark a route towards the A frame 60, to be followed by a submersible 70. The submersible itself has a 45° side scanning sonar, emitting wide band sonar transmission 68. The transmission will be reflected by the acoustic reflectors 64, with the reflected acoustic wave being directed back towards the submersible at 45° to the horizontal, resulting in each of the acoustic reflectors producing reflected signals that appear to be as strong as one another the receiver on the submersible.

If the sonar systems in use were bottom scanning sonars, the frame would be mounted horizontally rather than at an angle.

Figure 8:
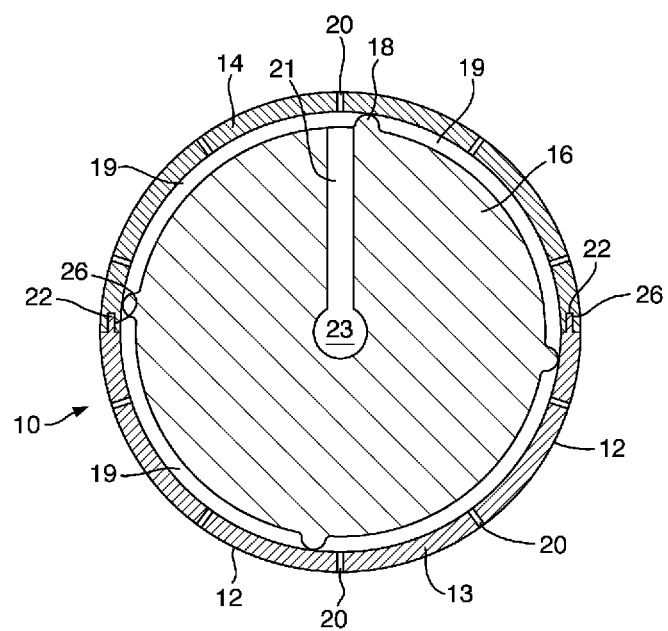
FIG. 8 is a cross section a spherical acoustic reflector having a central hole with an aluminium alloy shell.

FIG. 8 shows an embodiment of the invention in which an acoustic reflector 10 has a central hole. The general structure of the reflector is as in FIGS. 1 and 2, but in this case, a duct 21, about 10 mm in diameter, leads from the gap 19 to a central hole 23 in the core 16. The other parts are as discussed in FIGS. 1 and 2

When the reflector is immersed in water, water enters the gap 19, duct 21 and fills hole 23. Provided that the diameter of hole 23 does not exceed 10% of the diameter of the reflector the presence of water in the void 23 makes little difference to the general performance of the reflector, but it will change the frequency at which a peak response occurs, enabling the reflector to be tuned.

Figure 9:
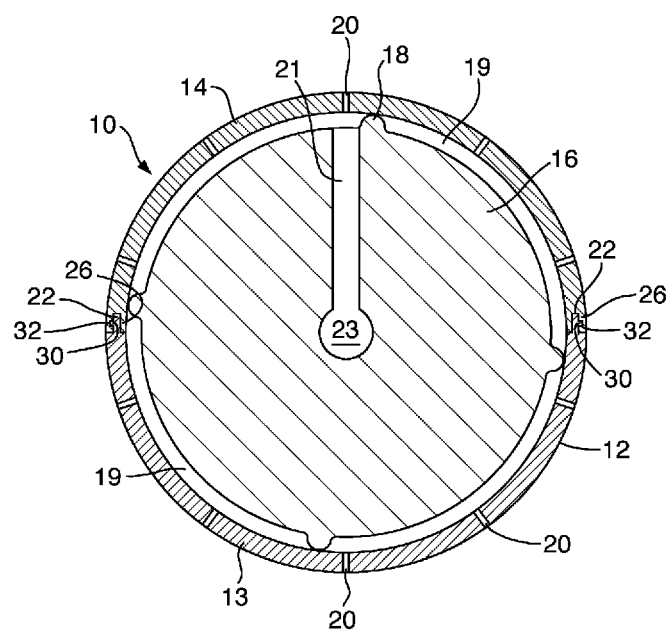
FIG. 9 is a cross section an acoustic reflector having a central hole in which the material of the shell of the acoustic reflector comprises 25% glass reinforced polyphthalamide.
Figure 10:
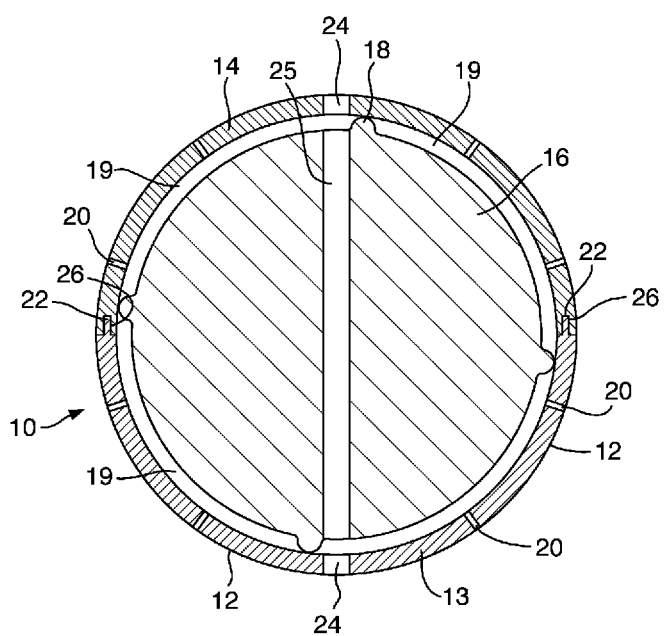
FIG. 10 is a cross section an acoustic reflector according to the invention with a central duct.

FIG. 9 is almost identical to FIG. 8, save that the shell of the acoustic reflector comprises 25% glass reinforced polyphthalamide. The components of the reflector are generally identical to those shown in FIG. 4C but with a duct 21, about 10 mm in diameter, leads from the gap 19 to a central hole 23 in the core 16. The other parts are as discussed in FIGS. 4A to 4C. In FIG. 10 showing a further variation on the reflector illustrated in FIGS. 1 and 2. Here the reflector 10 has a duct 25, about 10 mm in diameter, extending diametrically across the core 16. The shell 12 has two holes 24 through it, each opposite the entry points to the duct 25. These holes 24 are somewhat wider, at about 10 mm, than the other holes 20 in the shell. The holes 24 and duct 25 can receive a cord (not shown), say of nylon, which can be used to assist in the laying, placement or retention in position of the reflectors 10, or to tether the reflectors to one another.

In FIGS. 8 to 10, the pimples 18 and gaps 19 can be omitted so that outside of the core contact the inside of the shell. While this arrangement will still accommodate thermal expansion of the core, acoustic coupling of the core to the shell is less good than that in the arrangement illustrated, and is thus not a preferred way to implement the invention.

FIGS. 11 to 13 illustrate the construction and use of non-spherical reflectors. In each case the reflector has of circular cross section and is arranged and positioned such that sonar may interrogate that part of the shell that forms a circumference of the circular cross section.

Figure 11A:
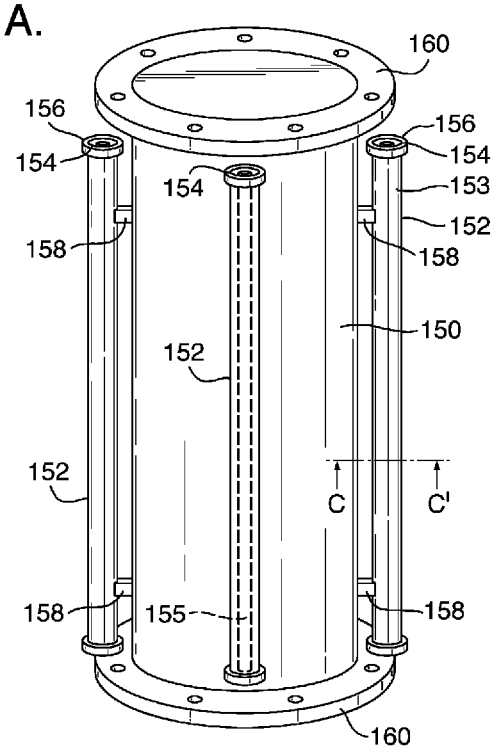
FIGS. 11A and 11B show the use of a tubular marker of the present invention marking a pipeline, FIG. 11B being a section on the line C-C' of FIG. 11A.
Figure 11B:
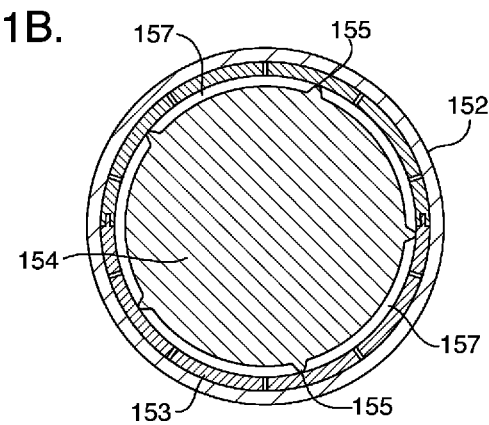

FIG. 11A shows a schematic diagram of a pipe section 150 fitted with a number of elongate tubular reflectors or markers 152 each according to the invention, each having an open ended tubular shell 153. FIG. 11B is a cross section of the reflector 152. The core 154 of the markers 152 is an elongate solid tubular section of silicon elastomer, but rather than having pimples as described in FIG. 1, the core 154 has been extruded with ridges extending along its outside surface to hold it in place within the tubular shell. Water able to enter the gaps 157 thus formed between the core 154 and the shell 153, in a similar way to that described in FIGS. 1, 2 and 4 above.

The open ends 156 of the markers 152 allow water freely to enter and leave the gaps 157. If the markers 152 have metal shells they would need to be isolated from the pipe sections 150 by conventional electrically insulating lugs 158, this would not be necessary in the more usual case where the cylindrical shells 153 were made of Zytel® or other non-conducting material. The pipe section 150 has conventional end flanges 160 with holes therein allowing it to be bolted to another pipe section. The pipe section with the markers can be prefabricated on land and joined by means of the bolt holes in the flanges 160 to another like fitted pipe. In this way, a pipe line fitted with acoustic makers can be assembled as part of the normal process for laying an underwater pipeline. As an alternative to or in addition to the core 153 may be formed with a central duct into which water may freely enter. However, the presence of the gap 157 filled with water enables far better acoustic coupling between shell 153 and core 154 than would be the case otherwise.

Although the tubular markers in FIGS. 11A and 11B have been described in relation to a pipe section, the markers can be applied to other objects, such as oil rig platforms, accommodation platforms for workers at sea, and other objects to be placed under water. For use in conjunction with sonar systems used in the oil and gas industry, typically the reflectors would be about 100 mm in diameter and the shell 25% glass fibre reinforced polyphthalamide shell, aluminium or aluminium alloy shells performing less well at the frequencies deployed. The shell could be constructed in two longitudinal halves, the core placed in one half and the two halves joined in the same way as discussed in the relation to the spherical shell of FIG. 4.

Figure 11C:
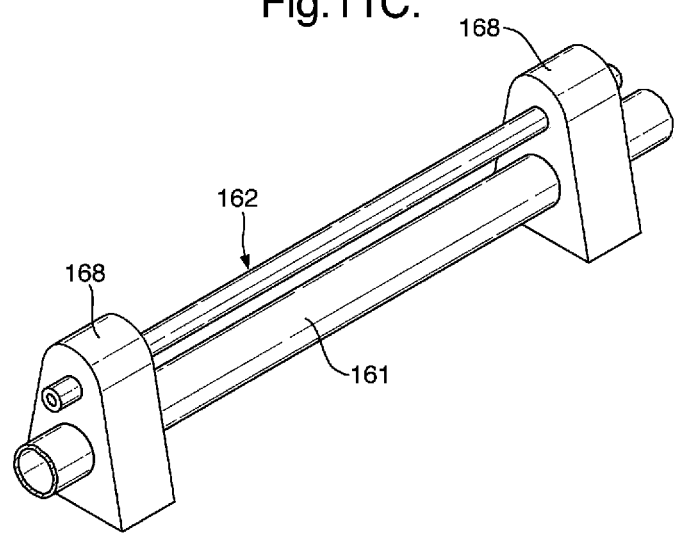
FIGS. 11C and 11D show the use of a tubular marker of the present invention to mark a gas pipe, FIG. 11D showing a section of the tubular marker section in more detail.
Figure 11D:
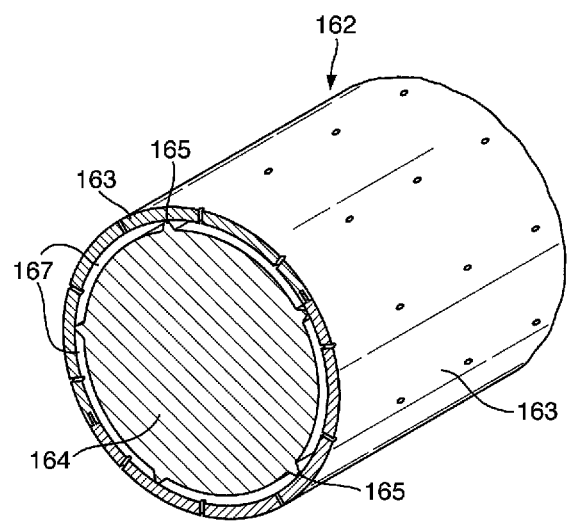

FIG. 11C is a schematic diagram of a plastic gas pipe 161 fitted with a number of elongate tubular reflectors or markers 162 each according to the invention. FIG. 11D is a cross section of the reflector 162. Each reflector or marker 162 has an open ended tubular shell 162. The core 164 of the markers 162 an elongate solid tubular section a silicon elastomer having been extruded with ridges extending along the length of its outside surface to hold the core in place within the tubular shell, with water able to enter the gaps 167 thus formed between the core and the shell, in a similar way to that described previously.

The tubular reflectors or markers 162 are mounted close to but separated from the gas pipe 161 in common supports 168. As an alternative to or in addition to the core 164 may be formed with a central duct into which water may freely enter. However, as before the presence of the gap 167, filled with water, enables far better acoustic coupling between the cylindrical shell 163 and core 164, than would be the case otherwise.

In operation the markers of FIGS. 11A to 11D work in exactly the same way as the other markers described herein. Acoustic waves transmitted from an acoustic source are incident on the tubular marker 152 or 162. Part of the wave passes through the shell 153 or 163 into the core 154 or 164, where it travels across the core to be reflected from the shell wall opposite the entry back across the core. Part of the wave travels around the shell wall and combines constructively with the part of the wave that was transmitted through the core to be reradiated outwards back towards the source of the original acoustic wave.

Although the tubular markers in FIGS. 11A to 11D have been described in relation to a pipe section, the markers can be applied to other objects, such as oil rig platforms, accommodation platforms for workers at sea, and other objects to be placed under water. For use in conjunction with sonar systems used in the oil and gas industry, typically the reflectors would be about 100 mm in diameter and the shell 25% glass fibre reinforced polyphthalamide shell, aluminium or aluminium alloy shells performing less well at the frequencies deployed. The shells 153 or 163 could be constructed in two longitudinal halves, the core placed in one half and the two halves joined in the same way as discussed in the relation to the spherical shell of FIG. 4.

The realisation that a plastic gas pipe or other non-ferromagnetic pipes can be marked in this way is a particularly important development as the is no other known cost effective way of satisfactorily of marking these once they have been placed underwater so that they can subsequently be traced. Ferromagnetic pipes can be traced using their magnetic signatures.

Another embodiment of the invention is shown in FIGS. 12A and 12B. A toroidal marker 170 constructed following the principals previously described. The marker has a shell 174 comprising two semi-circular cross sectioned halves 172 and 173, joined by a glued tongue 177 and groove 178 joint. A toroidal core 176 is formed of a moulded elastomer having pimples 180 on its outer surface to contact the inner surface of the shell and create a gap 182 between the inner wall of the shell and the core, typically this gap is about 1.3 mm. The shell 174 has a plurality of holes 175, which when the marker is immersed in water, permits water freely to flow from the outside of its shell 174 the shell into the core 176. The gap 182 forms a volume into which the core may expand when it is hot, and into or out of which water and air may freely enter and leave.

The shell in this example is aluminium or aluminium alloy, although any of the alternatives mentioned in relation to the earlier examples may be used.

Acoustic waves transmitted from an acoustic source are incident on the external surface of the marker 170. The waves are partly reflected and partly reradiated from the marker.

In this case the pimples may be replaced by moulded ridges akin to the ridges 157,167 in FIGS. 11A to 11D.

In FIG. 13 the lower portion 190 of a stanchion such as a bridge pier is shown extending below surface 191 into the sea bed 192. A series of toroidal acoustic markers 194A, 194B, 194C and 194D as described with reference to FIGS. 12A and 12B is mounted below the sea surface around the stanchion 190. Those markers 194A and 194B above the sea bed can be used to mark the stanchion 190. Currents will scour the sea bed preferentially around the stanchion 190, eventually lowering the sea bed level to 196 exposing the marker 194C which was initially below the sea bed. Detection of this marker 194C on interrogation by sonar will provide an early warning of scouring, and the need for possible attention.

As scouring continues and the sea bed drops further as indicated by line 198, a further marker 194D is exposed, which may indicate that a potentially dangerous situation has developed and the underwater mounting of stanchion 190 may need urgent attention.

The toroidal marker 170 can be mounted on the stanchion using one or a plurality of bars of the kind described in FIG. 5 made of the same material as the shell.

For some security and military applications it may be desirable that the reflector remains relatively invisible for a time after placement in the water. In order to achieve this using a reflector of the kind described herein, air has to be retained between the shell and the core until the time the reflector is intended to be detectable. By providing one larger hole in the shell, say 10 mm in diameter and ensuring that it is uppermost when the reflector is placed in the water; air is expelled rapidly when the plug therein dissolves.

Suitable plug materials include common salt (sodium chloride), oxides of alkali earths, calcium and boron, or magnesium (including alloys of magnesium that will react with salt water to form a soluble compound).

A further application of the invention includes monitoring the acoustic transmissibility of a body of water. By laying a number of acoustic reflectors according to the invention at increasing distances from a sonar source, the acoustic transmissibility of that body of water can be monitored by monitoring the reflected acoustic waves from the reflectors. As the transmissibility is reduced, say in rougher water, the reflectors furthest from the sonar source will no longer be seen. This can be useful when monitoring divers or fish stocks, since it will enable a distinction to be made between lack of response because there is no diver or fish to be seen, and a situation when turbulent or murky water is simply reducing the range of the sonar detector.

A problem has been identified sometimes if underwater acoustic reflectors of the kind described in WO2006/075167 namely that the reflected acoustic waves from within the core and from waves travelling around the shell can sometimes be entirely masked by acoustic waves reflected from the front of the shell. This is particularly true if an interrogating sonar has a long pulse length and is very close to the acoustic reflector. As a result, although the reflector can be 'seen', no identity information can be generated. The problem can be overcome by interrogating the reflector with a source of acoustic radiation in which the transmission length (in time) of an interrogating pulse is less than twice the diameter of the shell of an acoustic reflector divided by the average acoustic speed across the core. For example, as illustrated in this specification, if the core comprises RTV 12 with water freely entering and leaving the volume between the shell and the core, the average acoustic speed of acoustic waves within interior of the reflector after passing through the shell will be that of the RTV12 and water combination.

In some sonar systems transmissions with long pulses are used to enable the sonar system to gather substantial information about the surrounding environment. For use with an acoustic reflector of the kind the subject of this invention, it is desirable to intersperse a short pulse among the longer pulses. The shorter pulse has a pulse time less than twice the diameter of the shell of an acoustic reflector divided by the average acoustic wave speed across the water filled volume and core. Short pulses of this kind are interspersed regularly among longer pulses (say one pulse in four). Such a transmission pattern is shown in FIG. 14.

In FIG. 14, an underwater acoustic wave pattern 73 is transmitted from a sonar (not shown) towards a passive acoustic reflector of the kind shown in FIG. 1, 2 or 4. Shorter length pulses 72 are transmitted after every four longer pulses 71. Assuming the interior diameter of the reflector, across any water volume and the core, is 280 mm (in a spherical reflector of 300 mm diameter), and the average acoustic velocity across water volume and core is 1100 m/s, the maximum pulse length of the short pulse 72 is $5 \times 10^{-5}$ seconds, if the acoustic signal reradiated from the core is to be 'seen' by the interrogating sonar.

FIG. 15 illustrates the frequency response of an aluminium alloy shell underwater reflector according to the invention with an RTV12 core is shown (as described in FIGS. 1 and 2). The shell is 8.8 mm in thickness and 200 mm in diameter. There is an excellent response, better than −10 dB, at frequencies of incident acoustic waves between 4 and 80 KHz with the target strength (TS) optimum response of −3 dB at 62 KHz. This response is better than anything previously recorded for a passive underwater acoustic reflector. However at higher frequencies, above 100 KHz, the response curve is relatively flat and low, and at higher frequencies an acoustic reflector of the kind described with reference to FIG. 4 is significantly better. It should be noted that in the region marked X the response could not be measured using the transducers used to obtain the measurements as they were inoperable at these low frequencies. The curve shown therefore is based on data from a model, which shows secondary peak responses at 30 KHz and 20 KHz each with peak responses just below the maximum response at about 62 KHz. In the region between 160 and 230 KHz, marked Y, there is further uncertainty because of discontinuation between a low frequency transducers and a higher frequency transducer; the curve in this region represents a smoothing of the responses obtained; hover a peak at 200 KHz is consistent with model data.

Moving on to FIG. 16, the responses obtained from the back and front of the reflector are shown, with the same observation regarding the parts of the curves marked X and Y. In FIG. 16 it will be seen that below 80 KHz the echo from the back of the reflector is at least as strong as that from the front, meaning that in this range the reflector will produce significant information about the size of the reflector. It has been found that an excellent acoustic response is achieved from reflectors according to the invention with shell walls between 6 and 15 mm thick. While the exact response mechanism is not fully understood, it is thought that it is a combination of a response from waves passing through the shell and into the core being focussed and reflected from the rear of the shell constructively interfering with acoustic waves travelling around the shell wall, together with a resonant response mode in the shell itself. It has also been found that as shell thickness increases the frequency at which best response occurs tends to decrease as shell thickness decreases the best response occurs at increasing frequency; although reflectors with aluminium and aluminium alloy shells did not show as much variation in response for changes in wall thickness as the non-metal shelled reflectors discussed in relation to FIGS. 17 and 18.

For a reflector below 200 mm diameter with an aluminium or aluminium alloy shell, the response at low frequencies (below 100 KHz) decreases. Above 400 mm in diameter, although the response is very good, the reflector becomes is too large for practical deployment. Thus for reflectors to operate in a low frequency environment the ideal reflector diameter is between about 200 and 400 mm The reflectors with aluminium or aluminium alloy shells reflector are strong. Apart from making objects and passages for the underwater industry, practical applications include use in the fishing industry to mark nets and underwater pots and traps, and especially in the aviation industry to mark black boxes and other key components of aircraft. In that latter case the strength and lightness of the reflectors means that it is practical to for the device to be placed aboard an aircraft attached to the black box or other sensitive component. Should an aircraft ditch in the sea, identification and recovery of the component should be possible, in theory, at any time, a vast improvement on the present situation where finding black boxes and other components becomes very difficult after transponder batteries expire relatively quickly after ditching. In this latter context it is noted that the acoustic velocity of titanium is very close to that of aluminium and a titanium reflector will perform similarly to an aluminium or aluminium alloy reflector.

Changing the aluminium alloy from 6061T6 will impact on the specific performance figures measures, including the exact peak responses and their magnitude, but this would not detract from the principles underlying the invention. The suffix T6 indicates the accelerated age hardened process used in manufacture of the alloy used, even changing the age hardening will impact on performance.

The reflector illustrated in FIGS. 4A to 4C performs similarly at low frequencies to that of the aluminium alloy reflector whose performance is illustrated in FIG. 17 save that the peak response is −4 dB at just under 50 KHz. The left hand part of the curve marked X is based on model data again because of the inability of the test transducer to operate at these frequencies.

Moving on to FIGS. 18 and 19, and in contrast to what was found with the aluminium alloy shell reflector, the reflector of FIG. 4C also had a good response in the range 100 to 130 KHz again around −4 dB at 115 KHz, and between 360 and 400 KHz with the peak at 385 KHz. Further tests, not shown, show a good response between 650 and 690 KHz with a peak at 675 KHz, a further peak appearing to occur at 970 KHz. These results are particularly interesting as the frequencies of the best responses occur at the regular operating frequencies of sonar systems in the oil and gas exploration industry, making the reflectors shown in FIGS. 4A to 4C particularly good for use in that industry.

It is useful to compare the results shown is FIGS. 15 to 19 with those published in U.S. Pat. No. 5,822,272A (REAM) 13 Oct. 1998, it will be seen that they are significantly better.

The variation of the frequencies at which peak responses occur for various wall thickness in a 200 mm diameter reflector constructed as in FIG. 4C were compared. The primary response is that obtained at peak A in FIGS. 18 and 19, the secondary is that at peak B:

Shell Thickness 6.9 mm: Primary Median 124 KHz Secondary Median 438 KHz.
Shell Thickness 7.0 mm: Primary Median 119 KHz Secondary Median 425 KHz
Shell Thickness 8.0 mm: Primary Median 111 KHz Secondary Median 398 KHz
Shell Thickness 8.1 mm: Primary Median 111 KHz Secondary Median 380 KHz
Shell Thickness 8.8 mm: Primary Median 113.5 KHz Secondary Median 379 KHz
Shell Thickness 9.1 mm: Primary Median 101 KHz Secondary Median 360 KHz
Shell Thickness 10.0 mm: Primary Median 99 KHz Secondary Median 345 KHz
Shell Thickness 10.9 mm: Primary Median 115 KHz Secondary Median 330 KHz For shell thicknesses above 9 mm a further peak was observed between the two measured primary and secondary peaks.

It will be seen that increasing the shell thicknesses tends to decrease the frequencies at which peak responses occur, although this is not entirely consistent.

In each of the embodiments described the physical transmission of the acoustic waves in the reflector is as described above. At low frequency, it is believed that this mechanism may be enhanced by reverberation of the shell wall, although this is not proven; this may explain the better performance of metal shells at lower frequencies.

The invention claimed is:

1. An acoustic reflector for use underwater and comprising a shell surrounding a core said shell configured to permit acoustic waves at at least one frequency to at least partially enter and pass through the shell at one location, to pass into the core and to be reflected back from the shell opposite said one location, wherein the shell has one or more holes therein permitting water freely to enter and leave the inside of the shell when the reflector is deployed in water.

2. An acoustic reflector for use underwater and comprising a shell surrounding a core wherein the shell has one or more holes therein permitting water freely to enter and leave the inside of the shell when the reflector is deployed in water wherein said reflector has a circular cross section and comprises a shell surrounding a core, said shell permitting acoustic waves at one or more frequencies to pass, in part at least, through the shell into the core to be reflected back from the portion of the shell opposite the entry of the acoustic wave and in part to pass around within the shell to combine with the reflected wave and be reradiated from the reflector.

3. An acoustic reflector according to claim 2 wherein the core has a volume slightly less than the interior volume of the shell.

4. An acoustic reflector according to claim 3 wherein the core has a plurality of deformable raised portions on its surface, said raised portions contacting the inside of the shell and holding the core in position with respect to the shell and wherein a gap is formed between the interior of the shell and the core.

5. An acoustic reflector according to claim 3 wherein the interior of the shell may have a plurality of inward projections contacting the surface of the core and in which a gap is provided between the interior of the shell and the core.

6. An acoustic reflector according to claim 2, wherein the holes have water soluble plugs therein, said plugs dissolving when the reflector is immersed in water.

7. An acoustic reflector according to claim 2 wherein the holes are 1 mm to 2 mm in diameter.

8. An acoustic reflector according to claim 1 wherein the core comprises silicon based elastomeric material.

9. An acoustic reflector according to claim 8 wherein that the shell is a non-metal selected from the group comprising glass fibre reinforced polyphthalamide, epoxy impregnated carbon fibre, epoxy impregnated aramid fibre, epoxy impregnated poly(p-phenylene-2,6-benzobisoxazole) fibre, or epoxy impregnated polythene fibre.

10. An acoustic reflector according to claim 8 wherein the shell comprises a 25% glass fibre reinforced polyphthalamide shell.

11. An acoustic reflector according claim 10 wherein the shell is between 4 and 15 mm thick.

12. An acoustic reflector according to claim 1 wherein the shell is aluminium or an aluminium alloy.

13. An acoustic reflector according claim 12 wherein the shell wall is between 6 and 15 mm thick.

14. An acoustic reflector according to claim 2 wherein the core is precast.

15. An acoustic reflector according to claim 2 wherein the shell comprises two hemispheres joined together, the rim of hemisphere having a tongue engaging in a groove formed in the rim of the other hemisphere.

16. An acoustic reflector according to claim 1 wherein the reflector is coated with one or more layers of polyurethane around the outside of the shell.

17. An acoustic reflector according to claim 2 wherein the shell has a least one further hole or recess, said further hole or recess receiving an external bar.

18. An acoustic reflector according to claim 17 wherein the bar is made of the same material as the shell.

19. An acoustic reflector according to claim 17 wherein the reflector is one of at least two acoustic reflectors mounted in close proximity to one another to provide distance information to a scanning sonar system.

20. An acoustic reflector according to claim 17 wherein the reflector is mounted on a frame to reflect location identification information, such as letters and or numbers, to a scanning sonar system.

21. An acoustic reflector according to claim 1 in combination with a source of acoustic radiation which emits individual pulses of acoustic radiation for a time period less than twice the distance from the point of entry of the acoustic transmission into the core of the reflector divided by the acoustic velocity in the core.

22. An acoustic reflector according to claim 21 wherein said individual pulses occur regularly in a pattern of otherwise longer pulses.

23. An acoustic reflector according to claim 1 initially deployed with components of an aircraft.

24. An acoustic reflector according to claim 1 wherein the reflector is tubular.

25. An acoustic reflector according to claim 24 attached to a pipe section.

26. An acoustic reflector according to claim 24 attached to a non-ferromagnetic pipe.

27. An acoustic reflector according to claim 24 wherein the shell comprises an open ended tube, surrounding a core, the core having ridges on an outside surface contacting the tubular shell and forming a gap between the core and the shell and forming said volume and into or out of which water may freely enter and leave.

28. An acoustic reflector according to claim 1 wherein the reflector is substantially in the form of a toroid.

29. An acoustic reflector according to claim 28 wherein the reflector is mounted around an underwater object.

30. A spherical acoustic reflector for underwater deployment comprising a shell and a core; wherein the shell has one or more holes therein permitting water freely to enter and leave the inside of the shell when the reflector is deployed in water and wherein shell comprises two hemispheres, the rim of one hemisphere having a tongue engaging in a groove formed in the rim of the other hemisphere, and wherein when deployed water is present between the shell and the core.

* * * * *